United States Patent [19]

Molina

[11] 4,375,384

[45] Mar. 1, 1983

[54] METHOD FOR PENETRANT INSPECTION EMPLOYING AN ETCHANT PENETRANT

[75] Inventor: Orlando G. Molina, Westminster, Calif.

[73] Assignee: Rockwell International Corporation, El Segundo, Calif.

[21] Appl. No.: 355,402

[22] Filed: Mar. 8, 1982

[51] Int. Cl.³ .......................... C23F 1/02; B44C 1/22; C03C 15/00; C03C 25/06
[52] U.S. Cl. .................................. 156/626; 156/645; 156/656; 156/664; 252/301.19
[58] Field of Search .................. 156/626, 64, 655, 67, 156/656, 664, 645; 8/1, 76; 252/301.19

[56] References Cited

U.S. PATENT DOCUMENTS 2,635,329  4/1953  Forest et al. ...................... 156/64 X
2,740,700  4/1956  Fuller .............................. 156/626 X
3,171,768  3/1965  Levengood ....................... 156/663 X

*Primary Examiner*—William A. Powell
*Attorney, Agent, or Firm*—Charles T. Silberberg; Max Geldin

[57] ABSTRACT

A method for detecting cracks and surface discontinuities in an object which comprises applying to the surface of an object having a ground surface and smeared metal, an etchant penetrant solution capable of removing said smeared metal covering the openings of said cracks, cleaning said surface to remove said excess penetrant solution, and applying to said surface a developer coating containing a fluorescent material, the etchant remaining in the cracks being capable of destroying the fluorescence adjacent the cracks, and viewing the surface under ultraviolet light to reveal indications of cracks showing intensely black against a fluorescent background.

15 Claims, No Drawings

METHOD FOR PENETRANT INSPECTION EMPLOYING AN ETCHANT PENETRANT

BACKGROUND OF THE INVENTION

This invention relates to a process of non-destructive testing of bodies, particularly for the purpose of locating minute cracks or surface discontinuities from various causes such as stress cracks, quenching cracks, and the like. The invention is particularly concerned with a process of the above type where the object contains ground out areas having smeared metal, and which removes the smeared metal and reveals othr cracks or surface discontinuities.

In many instances, surface cracks in parts or objects are removed by grinding out appropriate areas in welds or parent material. It is accordingly then necessary to remove smeared metal or material remaining on the surface and to locate any residual cracks not previously removed by the grinding operation.

U.S. Pat. No. 3,564,249 discloses a reverse penetrant method and means comprising applying to the surface of a specimen to be inspected, a liquid dye penetrant containing a daylight visible dye, removing excess penetrant from the surface of the specimen, and applying to the surface a developer coating containing a fluorescent material and when viewed under fluorescent light the coating fluoresces uniformly over the surface with dark dye traces whereever residual dye penetrant is entrapped is surface defects, and which stand out in sharp contrast with the brilliance of the fluorescing background coating.

It is an object of the present invention to detect surface cracks in bodies, the surface of which has been previously ground to remove surface cracks, with smeared metal remaining on the surface. Another object is to remove surface cracks remaining beneath the smeared metal by removing such smeared metal by a penetrant solution followed by application of a reversal developer of the type noted above. A still further object is the provision of a process of the type noted above by a simple three step operation employing a penetrant which also functions as an etchant, in conjunction with a reversal developer.

SUMMARY OF THE INVENTION

The above objects and advantages are achieved, according to the invention, by applying to the surface of an object which has been previously ground to remove superficial surface cracks and leaving smeared metal on such surface, an etchant-penetrant, which contains no dye, but which is chemically active and capable of removing the smeared metal from the surface to uncover other defects, removing excess etchant-penetrant from the surface of the object and applying to the surface of the object a reversal developer containing a fluorescent material, of the type noted in the above patent, to form a coating of the developer on the surface. When subjected to ultraviolet light, the residual entrapped etchant-penetrant solution in the cracks forms black indications against the fluorescent background of the developer coating.

The black indications of defects are formed in the fluorescent developer coating by the chemical action of the etchant-penetrant in the entrapments within the defects, locally destroying the fluorescence of the developer coating by chemical action.

Thus as an essential feature of the invention, the etchant-penetrant performs the dual function as the means for removing the smeared metal from the openings of any defects below such smeared metal following grinding, and also functions as the penetrant which reveals the presence of any cracks still remaining in the area being reworked by grinding, as result of its chemical action with the reversal developer.

The present invention is of considerable importance since it provides an efficient time saving process where smeared metal must first be removed from the surface following a grinding operation, prior to penetrant inspection.

On the other hand, if an etchant removal step is employed for removing smeared metal from ground surfaces, followed by use of a conventional penetrant process, wherein a penetrant composition containing a fluorescent dye is first applied, excess penetrant removed and a developer composition is applied to the part surface, small amounts of etchant which may be still entrapped inside of cracks can readily affect and destroy the performance of such conventional penetrant inspection process, thus allowing cracks to remain undetected in critical parts.

Thus, while in the process of above U.S. Pat. No. 3,564,249, and in conventional processes, a penetrating solution containing a non-fluorescent dye or a fluorescent dye is used to produce entrapments of the penetrating liquid into defects open to the surface of parts or assemblies, followed by application of a fluorescent or contrasting developer coating, in the present invention the penetrating solution is chemically active, contains no dyes and produces indications of the defects by using a developer coating containing a fluorescent dye as in the above patent, but the purpose of the chemically active dye-less penetrant and its reaction with the developer coating are entirely different in both performance and composition from the above patent.

Thus, briefly the invention is directed to a method for detecting cracks and surface discontinuities in an object which comprises applying to the surface of an object which has been ground and contains smeared metal, an etchant-penetrant solution capable of removing said smeared metal from adjacent the openings of said cracks, cleaning said surface to remove said smeared metal, and applying to said surface a developer coating containing a fluorescent material, the etchant remaining in the cracks being capable of destroying the fluorescence adjacent the cracks, and viewing the surface under ultraviolet light to reveal intensely black crack indications against a fluorescent background.

DETAILED DESCRIPTION OF THE EMBODIMENTS OF THE INVENTION

In the invention process, the liquid penetrant containing the etchant functions to remove smeared metal and also to fill the cracks with solution, the etchant-penetrant solution destroying the fluorescent dye in the developer coating at the cracks. The penetrant exudes from the cracks and simultaneously destroys the fluorescent developer and also magnifies the size of the defect clearly outlined against the fluorescent background of the developer coating. The etchant solutions which can be employed can be acidic or basic depending upon the metals to be etched.

Etchant solutions either basic or acidic also have the property to interact with the fluorescent reversal developer coating by destroying the fluorescence of the coating covering the defects in the surface. Metals which can be inspected according to the etchant process of the invention include nonferrous or ferrous metals. Thus metals such as aluminum, steel, nickel, titanium, and alloys thereof can be utilized.

Both acid and basic penetrant formulations can be employed.

Thus, specific examples of typical acid penetrant formulations include, for example, hydrochloric acid, sulphuric acid, nitric acid and the like, and mixtures thereof.

Hydrogen peroxide can be added to such acid formulations to aid in destroying the fluorescene of the fluorescent dye from the reversal developer at the cracks containing the liquid penetrant.

Basic formulations or basic penetrants can also be employed. Generally these are the typical formulations for etching smeared aluminum and aluminum alloys. For this purpose, alkalies such as caustic soda or sodium hydroxide is employed and a small amount of chromic acid is added which functions to kill or destroy the fluorescence of the reversal developer and does not affect the etching properties of the formulation. The above property of chromic acid permits this material to be used in many other basic etchant formulations as well as acid formulations which otherwise do not have the ability to destroy fluorescence and produce black indications of cracks against the fluorescent reversal developer used in practicing the invention.

The following are examples of acid penetrant formulations according to the invention:

For removing smeared metal from INCO 718, INCOLOY 903, INCOLOY 88, A-286, and 21-6-9 Metal alloys. (nickel alloys)
Composition A By volume
50 pts. Hydrogen Peroxide ($H_2O_2$)(30% solin)
50 pts. Hydrochloric Acid (HCl)(37% aq. solin)
Composition B By volume
20 pts. Hydrogen Peroxide ($H_2O_2$)(30% aq. solin)
80 pts. Hydrochloric Acid (HCl)(37% aq. solin)

FOR REMOVING SMEARED METAL FROM HAYNES 188 AND INCO 625-Fe BASE ALLOYS

Composition C By Volume
3 pts Hydrochloric acid (HCl)(37% aq. solin)
1 pt Nitric Acid ($HNO_3$)(70% aq. solin)
1 pt Sulphuric Acid ($H_2SO_4$)(98% aq. solin)

The following are examples of basic penetrant formulations employed according to the invention:
Composition D
1 gram caustic soda (NaOH)
100 ml water
1 gram chromic acid ($CrO_3$)
Composition E
3 grams caustic soda (NaOH)
100 ml water
3 grams chromic acid ($CrO_3$)

Other examples of acid and basic formulations which can be employed according to the invention are listed below:
Composition F
Cupric chloride: 15 g
Ferric chloride: 15 g
HCL (37% solin): 200 cc
$H_2O_2$: 100 cc It should be understood that there are many variations of the etchant solution which can be used for practicing the invention in addition to those noted below, the basic requirements for an etchant-penetrant for use according to the invention being that the solution must remove smeared metal by etching action and the solution must kill or destroy the fluorescence of the reversal developer applied as a coating following removal of excess penetrant from the part surface.

Following the application of the etchant-penetrant to the smeared metal surface, the excess penetrant is removed from the test surface by any suitable means, e.g. by wiping off excess etchant with a clean cloth moistened with water and allowing the metal surface to dry. Preferably the test surface is not cleaned so completely as to remove residual etchant-penetrant entrapped within surface cracks or defects. Preferably, after the above noted cleaning step the test surface should be dried, either using heat or air blasting when convenient to accelerate the same.

After the above steps, the test surface is coated with a developer containing a fluorescent material, of the types disclosed in above U.S. Pat. No. 3,564,249, and which is incorporated herein by reference. Various fluorescent dyes are incorporated into the developer including the dye marketed as Fluorol 7GA and Morton Fluorescent Yellow G, Hudson Yellow D-250, as well as other fluorescent dyes such as those marketed as Calcofluor Yellow, Azosol Brilliant Yellow 6 GF; Rhodamine B, Phodamine 6 GDN, Calcofluor White RW, Blancophor White, AW, Auramine and Eosine G, and water soluble fluorescent dyes such as Blancophor FFG.

The invention process can be practiced using slurry-type developers having a powder, such as talc, in suspension, and incorporating a small quantity of fluorescent material combined therewith before application of the developer to the test surface.

Thus, aqueous or non-aqueous type developers can be employed and which can contain a solvent such as an aliphatic alcohol, e.g. isopropyl alcohol, or chlorinated solvents such as chlorinated hydrocarbons, e.g. trichlorothane. Thus, for example the wet non-aqueous developer composition of my U.S. Pat. No. 3,748,469, consisting essentially of isopropyl alcohol, talc and glycol monobatyl either can be employed.

Amending to U.S. application Ser. No. 939,550 of Orlando G. Molina, filed Sept. 5, 1978, a set non-aqueous developer can be used comprising a vehicle such as an alcohol, e.g. isopropyl alcohol, or a halocarbon, e.g. 1,1,1 trichloroethane, a powder, particularly talc, and a small amount of a liquid surfactant which is miscible with the liquid organic vehicle, such as a nonionic oxyalkylated aliphatic alcohol, and particularly ethoxylates of a mixture of linear secondary eliphatic alcohols, represented by the materials marketed as the Tergitols 15-S-3 to 15-S-12.

More particularly, one class of such nonionic solvents or carriers can be defined as straight chain, primary, aliphatic oxyalkylated alcohols, generally in the form of mixtures thereof, wherein the primary aliphatic alcohols can have from 8 to 20 carbon atoms, preferably 10 to 18 carbon atoms, and the oxyalkyl groups are ethylene oxide and propylene oxide, preferably in the form of a mixture thereof.

One group of nonionic surfactants within the class of materials defined immediately above is a cogeneric mixture of compounds represented by the formula:

$$R-O(A)H \qquad (1)$$

wherein:

R is an essentially linear alkyl group having from 10 to 18 carbon atoms, with the priviso that at least 70 weight percent of said compounds in said mixture have an R of from 12 to 16 carbon atoms, and A is a mixture of oxypropylene and oxyethylene groups, said oxypropylene and oxyethylene groups being from 55% to 80% of the total weight of the compounds, the oxypropylene to oxyethylene ratio of said total weight being from 0.85:1 to 2.75:1, preferably 1.25:1 to 2.25:1.

Another preferred class of condensation products or oxylkylated alcohols within the above definition are those wherein the aliphatic alcohols of the oxyalkylated alcohols, or R in the above formula, ranges from 12 to 18 carbon atoms, and the total number of ethylene oxide and propylene oxide groups in the mixture thereof, or designated A in the above formula, ranges from about 4 to about 14.

A class of particularly preferred nonionic biodegradable surfactants for the wet nonaqueous developer compositions according to the present invention are ethoxylates of a mixture of linear secondary aliphatic alcohols, with the hydroxyl groups randomly distributed, the linear aliphatic hydrophobic portion of such alcohols being a mixture of alkyl chains containing in the range from 10 to 17 carbon atoms, preferably from 11 to 15 carbon atoms, and containing an average of from 3 to 12 moles of ethylene oxide.

The above particularly preferred class of nonionic biodegradable surfactant employed in the developer compositions of the invention is a mixture of compounds which can be represented by the formula:

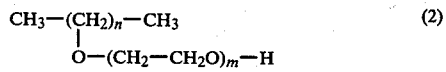

(2)

where n is in the range from 9 to 13, and m is 3 to 12.

Although preferably each of the above-defined surfactants is formed of a mixture of two or more linear aklyl hydrophobic chains ranging from $C_{11}$ to $C_{15}$, as noted below the surfactant can contain a single such chain formed from a single secondary aliphatic alcohol of the types described below.

The linear alkyl hydrophobic portion of the above defined surfactant is a mixture of $C_{11}$ to $C_{15}$ linear alkyl chains, and can be derived from a mixture of $C_{11}$ to $C_{15}$ aliphatic secondary alcohols, for example the secondary undecyl, dodecyl, tridecyl, tetradecyl and pentadecyl alcohols. The hydrophilic portion of the surfactant is a polyoxyethylene chain randomly attached to any carbon atom of the linear alkyl hydrophobic chain, other than to the terminal carbon atoms thereof, through an ether linkage. It will accordingly be understood that the specific carbon atom in the alkyl hydrophobic chains to which the hydrophilic polyoxyethylene chain is attached will become a —CH— group. Such hydrophilic polyoxyethylene chain is generally expressed in terms of average number of moles of ethylene oxide.

Illustrative examples of biodegradable nonionic surfactants of the types defined in the above formula are those consisting of a mixture of ethoxylates of from 11 to 15 carbon atoms in the aliphatic hydrophobic chain, and which have an average of 3, 5, 7, 9 and 12 moles of ethylene oxide, respectively, as the hydrophil.

Materials corresponding to these five examples of biodegradable nonionic surfactants are marketed, respectively, as:

Tergitol 15-S-3
Tergitol 15-S-5
Tergitol 15-S-7
Tergitol 15-S-9
Tergitol 15-S-12

In each case of the Tergitol S series of surfactants listed above, the number to the left of the "S" indicates a hydrophobic aliphatic chain of from 11 to 15 carbon atoms derived from a mixture of alcohols on $C_{11}$ to $C_{15}$ backbone chains, and the number to the right of the "S" designates the average number of moles of ethylene oxide as the hydrophil. Thus, for example, Tergitol 15-S-5 is a mixture of linear aliphatic alcohols in the $C_{11}$ to $C_{15}$ range ethoxylated with an average of 5 moles of ethylene oxide. All of these commercially marketed Tergitol S series of surfactants are water soluble, except for Tergitol 15-S-3, which is essentially water insoluble. Mixtures of these materials can also be employed in providing the nonaqueous developer compositions of the invention, such as a mixture of the above Tergitols 15-S-5 and 15-S-3; a mixture of 15-S-3 and 15-S-9; and a mixture of 15-S-5 and 15-S-9.

The amount of fluorescent dye contained in the developer composition can range from about 0.01 to about 5.0% by weight of the composition. Higher levels of fluorescent dyes can be used.

The method of application of the invention process is as follows:

The metal specimen or object is ground down to remove surface cracks, leaving smeared metal.

The etchant-penetrant composition or solution of the invention is then applied to the metal surface containing smeared metal and the solution is allowed to etch the surface for a period of about 165 minutes.

Excess etchant is then removed from the surface employing a clean coth moistened with water and the metal surface allowed to dry.

Reversal developer is then applied as for example by spraying a fine coating of the developer on the previously etchant-treated metal surface, and the developer coating is permitted to dry.

The coating is then inspected for indications of cracks by subjecting the coating to black light or ultraviolet illumination in a darkened area. The indications of cracks appear as black indications against a fluorescent, e.g. yellow-green, fluorescent background, depending upon the dye utilized in the developer composition.

It will be noted that the process of the present invention can be employed for locating cracks in any surface of any object whether or not the surface has been previously ground.

The following are examples of practice of the invention.

EXAMPLE I

A sample of INCO 718, a nickel base alloy was ground to remove surface cracks and was then cleaned by treatment with water followed by acetone, leaving smeared metal on the surface of the specimen.

The cleaned specimen was then immersed in the acid etchant composition A above, excess etchant was wiped off with a clean cloth moistened with water and the metal surface allowed to dry in air.

A reversal non-aqueous developer, composition G below was applied by spraying a fine coating onto the previously etchant treated metal surface.

| Composition G | by Weight |
|---|---|
| Tergitol 15-S-9 | 1.0 |
| Isopropyl alcohol | 81.97 |
| MP 15-38 Talc | 17.0 |
| Calcoflour White RW | 0.02 |
| Morton Yellow G dye | 0.01 |
| | 100.0 |

In the above composition, Tergitol 15-S-9, is an oxyalkylated alcohol surfactant described above, and the non-aqueous developer is that which is described in my copending application Ser. No. 939,550, filed Sept. 8, 1978, to which the Calcoflour White and Morton Yellow dyes were added.

The surface was then inspected for indications of cracks by means of black light illumination. Jet black indications of the cracks were observed against a yellow green fluorescent background.

EXAMPLE II

The procedure of Example I was repeated but employing as the acid etchant composition B above.

The results obtained were similar to those of Example I above.

EXAMPLE III

The procedure of Example I was repeated except employing as the metal specimen Haynes 188, an iron base alloy, and utilizing the acid etchant composition C above.

Results obtained were similar to those of Example I.

EXAMPLE IV

The procedure of Example I was repeated except employing as the metal specimen stainless steel 316-L and utilizing as the acid etchant composition F above.

The results obtained were similar to those of Example I above.

EXAMPLE V

The procedure of Example I was followed except employing as the specimen the aluminum alloy 2024 aluminum, and utilizing as the etchant the basic etchant composition D.

Results similar to those noted in Example I were obtained.

In all of Examples I to V above, the acid or basic etchant functions to remove smeared metal by the etching action, and the solution also functions to destroy the fluorescence of the reversal developer at the cracks containing the acid or basic etchant.

EXAMPLE VI

The process of Example I was repeated but employing a metal specimen of INCO 718 which was not previously ground and which did not contain smeared metal.

When viewed under black light, results similar to those of Example I were obtained, indicating that the process of the invention is applicable employing an acid or basic etchant followed by a reversal developer, for surfaces of specimens which were not previously ground.

EXAMPLE VII

The process of Example I was repeated through the acid etchant step.

Thereafter the surface of the specimen was treated with a red visible dye penetrant composition, namely formulation No. 2 of my U.S. Pat. No. 4,191,048, and containing a red visible dye, followed by removal of excess red visible penetrant and application of the reversal developer of Example I. The formulations of this patent are incorporated herein by reference.

The red visible dye formulation of this patent is noted below.

| COMPOSITION H | |
|---|---|
| Components | Parts by Volume |
| Automate Red B (dye) | 1 |
| Tergitol 15-S-9 (surfactant) | 3 |
| Exxon Isopar M Solvent (extender) | 8 |

Automate Red B is a single phase liquid and a red visible azo dye containing $C_7H_{15}$ beta naphthols.

Isopar M solvent is an isoparaffin having a carbon chain ranging from about 10 to about 17 carbon atoms and preferably is a mixture of such isoparaffins.

The system was viewed under black or ultraviolet light in one case and white light in another case.

The results show the acid etchant interferes with the effectiveness of the red visible dye penetrant in producing indications of cracks, but when used with the reversal developer and black light the effectiveness of the penetrant developer for detecting cracks is not diminished by the acid etch solution.

From the foregoing, it is seen that the invention provides a simple, rapid and reliable, non-destructive inspection process, particularly designed for use on parts following grinding and having smeared metal, which involves application of an etchant penetrant which can be acidic or basic, in conjunction with a reversal developer containing a fluorescent dye, the penetrant-etchant being capable of removing smeared metal and also functioning to destroy the fluorescence of the reversal developer at the mouth of the cracks in which the penetrant action is retained, to provide black indications of cracks against a fluorescent background.

I claim:

1. A method for detecting cracks and surface discontinuities in an object which comprises applying to the surface of an object having a ground surface and smeared metal, an etchant penetrant solution capable of removing said smeared metal from adjacent the openings of said cracks, cleaning said surface to remove the excess etchant penetrant, and applying to said surface a developer coating containing a fluorescent material, the etchant remaining in the cracks being capable of destroying the fluorescence adjacent the cracks, and viewing the surface under ultraviolet light to reveal black crack indications against a fluorescent background.

2. The method of claim 1, said etchant penetrant solution being an acid etchant.

3. The method as defined in claim 1, said etchant penetrant solution being a basic etchant.

4. The method as defined in claim 1, said developer coating comprising a non-aqueous reversal developer containing an organic solvent, a developer powder and a fluorescent dye.

5. The method as defined in claim 1, said metal being selected from the group consisting of aluminum, steel, titanium and nickel, and their alloys.

6. The method as defined in claim 1, said developer containing a small amount of nonionic surfactant, said surfactant being an oxyalkylated alcohol surfactant.

7. The method as defined in claim 2, said acid etchant comprising a mixture of hydrogen peroxide and hydrochloric acid.

8. The method as defined in claim 3, said basic etchant comprising a mixture of alkali and chromic acid.

9. A method for detecting cracks and surface discontinuities in an object which comprises applying to the surface of an object an etchant penetrant solution, cleaning said surface to remove excess penetrant, and applying to said surface a developer coating containing a fluorescent material, the etchant remaining in the cracks being capable of destroying the fluorescence adjacent to the cracks, and viewing the surface under ultraviolet light to reveal black crack indications against a fluorescent background.

10. The method as defined in claim 6, wherein said surfactant consists of ethoxylates of a mixture of alcohols having the formula:

$$CH_3-(CH_2)_n-CH_3$$
$$|$$
$$O-(CH_2-CH_2O)_m-H$$

where n is in the range from 9 to 13 and m is an average of 3 to 12.

11. The method as defined in claim 4, said organic solvent being an oliphatic alcohol or a chlorinated solvent.

12. The method of claim 10, said etchant penetrant solution being an acid etchant.

13. The method as defined in claim 10, said etchant penetrant solution being a basic etchant.

14. The method as defined in claim 9, said developer coating comprising a non-aqueous reversal developer containing an organic solvent, a powder and a fluorescent dye.

15. The method as defined in claim 14, said organic solvent being an oliphatic alcohol or a chlorinated hydrocarbon and said powder being talc.

* * * * *